(12) United States Patent
Signorino et al.

(10) Patent No.: US 11,857,706 B2
(45) Date of Patent: Jan. 2, 2024

(54) DISPLAY APPARATUS FOR A DOMESTIC APPLIANCE

(71) Applicant: emz-Hanauer GmbH & Co. KGaA, Nabburg (DE)

(72) Inventors: Manfredi Signorino, Wackersdorf (DE); Martin Brabec, Nabburg (DE)

(73) Assignee: emz-Hanauer GmbH & Co. KGaA, Nabburg (DE)

( * ) Notice: Subject to any disclaimer, the term of this patent is extended or adjusted under 35 U.S.C. 154(b) by 0 days.

(21) Appl. No.: 17/411,670

(22) Filed: Aug. 25, 2021

(65) Prior Publication Data

US 2022/0072189 A1 Mar. 10, 2022

(30) Foreign Application Priority Data

Sep. 10, 2020 (DE) .......................... 102020123648.4

(51) Int. Cl.
*A61L 9/20* (2006.01)

(52) U.S. Cl.
CPC .......... *A61L 9/205* (2013.01); *A61L 2209/11* (2013.01); *A61L 2209/12* (2013.01)

(58) Field of Classification Search
CPC ........................... A61L 9/205; A61L 2209/11; A61L 2209/111; A61L 2209/12; A61L 9/02; A61L 9/20; A61L 9/04; A61L 9/015; A61L 9/16; A61L 9/18; F25C 2400/10
See application file for complete search history.

(56) References Cited

U.S. PATENT DOCUMENTS

| | | | |
|---|---|---|---|
| 6,286,330 B1 * | 9/2001 | Kopf ..................... | F25D 17/042 62/314 |
| 9,492,576 B1 * | 11/2016 | Cudak ...................... | A61L 2/10 |
| 9,803,910 B2 * | 10/2017 | Kim ......................... | B01J 23/72 |
| 10,722,605 B2 * | 7/2020 | Kim ....................... | B01D 53/04 |
| 2008/0016898 A1 * | 1/2008 | Vestal .................... | B01D 46/44 62/317 |
| 2014/0245771 A1 | 9/2014 | Kim et al. | |
| 2017/0216475 A1 | 8/2017 | Park et al. | |
| 2018/0259242 A1 * | 9/2018 | Sumihiro ................ | F25D 11/00 |

FOREIGN PATENT DOCUMENTS

| | | |
|---|---|---|
| CN | 202905062 | 4/2013 |
| CN | 104575334 | 4/2015 |
| CN | 204943702 | 1/2016 |
| CN | 209087285 | 7/2019 |
| JP | 2020-521556 | 7/2020 |
| KR | 20-0389142 | 7/2005 |
| KR | 10-2011-0049465 | 5/2011 |

OTHER PUBLICATIONS

LeahRae et al. ("Pint-sized Air Purifier Equipped with LED Display Screen" Year: 2013). (Year: 2013).*
Official Action with Machine Translation for Korea Patent Application No. 10-2021-0120609, dated Dec. 10, 2022, 10 pages.
Official Action (with English translation) for China Patent Application No. 2021110538523, dated Mar. 23, 2023, 13 pages.

* cited by examiner

*Primary Examiner* — Joshua L Allen
*Assistant Examiner* — Shizhi Qian
(74) *Attorney, Agent, or Firm* — Sheridan Ross P.C.

(57) ABSTRACT

The invention relates to a display apparatus for a domestic appliance, at least one air treatment apparatus being integrated in the display apparatus, the at least one air treatment apparatus comprising a first radiation source device by means of which a fluid, in particular air, passing through a passage channel can be treated.

13 Claims, 3 Drawing Sheets

DISPLAY APPARATUS FOR A DOMESTIC APPLIANCE

CROSS-REFERENCE TO RELATED APPLICATION

This application claims the benefit of German Patent Application No. 10 2020 123 648.4 filed Sep. 10, 2020, the entire contents of which are hereby incorporated herein by reference.

FIELD

The invention relates to a display apparatus for a domestic appliance and to a domestic appliance comprising a display apparatus, a housing and a container device provided therein.

BACKGROUND

Such a domestic appliance can be, for example, a refrigerator or a freezer. In this case, the container device would be the container to be cooled. Furthermore, the domestic appliance could be a dishwasher, a washing machine or a similar appliance. In such a case, the container device would be a tub in which the articles to be washed and the washing liquid are located. For the manufacturers of such domestic appliances, it is desirable to attach a display apparatus to the domestic appliance that is used to display specific information. For example, a logo can be presented by means of a display apparatus.

As the operating time increases, it is often desirable for the air located in the container device to be treated. Microorganisms present in the air—such as viruses, bacteria, yeasts and moulds—can endanger human health, contaminate raw materials and spoil food. Furthermore, the air can contain gases, liquids and solids which leave an unpleasant odour. However, a permanent opening for air exchange is often not desirable, since cooling power or washing liquid can escape from the container device. So far, carbon-based filters have been used, which have to be replaced at regular, relatively short intervals.

SUMMARY

The object of the present invention is to provide a display apparatus for a domestic appliance that overcomes the disadvantages mentioned. Another object of the invention is to provide a domestic appliance having a display apparatus.

This object is achieved by the subject matter of claims 1 and 10. The dependent claims comprise preferred embodiments.

According to the invention, a display apparatus for a domestic appliance is provided, at least one air treatment apparatus being integrated in the display apparatus, the at least one air treatment apparatus comprising a first radiation source device by means of which a fluid, in particular air, passing through a passage channel can be treated.

By integrating the air treatment apparatus into the display apparatus, a single apparatus is provided which can achieve two tasks in an effective manner. This provides a compact apparatus which can be easily accommodated in the domestic appliance. A fluid of this type is advantageously a mixture of gases, liquids, solids and microorganisms. In particular, this fluid is air. The domestic appliance advantageously comprises a housing and a container device provided therein. The air treatment apparatus can preferably be arranged on or in the housing of the domestic appliance. In contrast to carbon-based filters, an air treatment apparatus of this type does not have to be serviced or has to be serviced at significantly longer intervals.

According to a preferred embodiment, at least one air flow device is provided, by means of which an air flow or a fluid flow into and/or out of the air treatment apparatus can be generated. The air flow or the fluid flow advantageously passes through the at least one air treatment device or through the passage channel. Advantageously, an air flow or a fluid flow into and/or out of the container device can be generated by means of the at least one air flow device. The air in the container device can thus advantageously be treated, i.e. cleaned and/or disinfected, by means of the at least one treatment device.

According to a preferred embodiment, the air treatment apparatus comprises a photocatalysis device. The first radiation source device preferably emits electromagnetic radiation. The photocatalysis device can preferably be exposed to at least part of the electromagnetic radiation in order to produce a photocatalytic reaction.

According to a preferred embodiment, the photocatalysis device comprises at least one photocatalytic material. The photocatalysis device preferably comprises a photocatalysis surface which comprises at least one photocatalytic material. The photocatalytic material is preferably integrated in the photocatalysis surface. At least the photocatalysis surface preferably consists at least partially of at least one photocatalytic material. The photocatalysis surface of the photocatalysis device advantageously comprises portions made of a photocatalytic material. Preferably, at least the photocatalysis surface of the photocatalysis device consists entirely of a photocatalytic material. The photocatalysis surface is preferably exposed to the electromagnetic radiation from the radiation source device.

The photocatalytic material of the photocatalysis device is preferably a semiconductor. Semiconductors are usually described by the so-called band model and comprise a conduction band and a valence band, which are energetically separated from one another by the so-called band gap. The size of the band gap varies, in each case, with the individual semiconductor material. The valence band and the conduction band are occupied by electrons according to the Fermi distribution. Accordingly, at zero temperature, the valence band is occupied and the conduction band is unoccupied. An incident photon can create an electron-hole pair if the energy of the photon is greater than or equal to the energy difference in the band gap. By means of the mobile electrons in the conduction band, a chemical or photocatalytic reaction can advantageously take place on the surface of the photocatalytic material. A particle of the air is advantageously reduced in this case. Such a particle can preferably be a molecule, an ion or an atom. This reduction can already change the chemical properties of specific components so that they no longer cause an unpleasant odour or can be removed more easily, for example by washing off. Furthermore, free radicals can be created by means of the chemical or photocatalytic reaction. Free radicals are molecules, ions, or atoms with an unpaired electron and are highly reactive. These free radicals can advantageously react with the undesired microorganisms and gases in the air and kill them or convert them into other gases. The air is thus cleaned of undesired microorganisms and undesired gases, which can cause unpleasant odours. According to a preferred embodiment, the photocatalytic material is titanium(IV) oxide, titanium dioxide, TiO$_2$. The air can therefore be cleaned and also disinfected. The common carbon-based filters cannot ensure disinfection of the air.

According to a further advantageous embodiment, the first radiation source device comprises at least one radiation source. The at least one radiation source is preferably a light-emitting diode (LED). The first radiation source device advantageously emits electromagnetic radiation with a wavelength of less than 400 nm. The first radiation source device advantageously emits UV radiation. The at least one radiation source is preferably a UV LED. A large number of radiation sources is preferably provided. The emitted electromagnetic radiation, preferably in the form of UV radiation, strikes the photocatalysis device or the photocatalysis surface and causes the above-described photocatalytic reaction. In an advantageous use of titanium dioxide, TiO$_2$, irradiation with UV radiation results in the generation of an electron-hole pair and the described chemical or photocatalytic reaction. Titanium dioxide can preferably remove natural and artificial impurities in air and water by exposure to UV radiation by reducing the oxygen in the air and oxidizing (mineralising) the impurities into environmentally friendly end products. Furthermore, the surface of titanium dioxide can advantageously become superhydrophilic by absorption of UV radiation. The first radiation source device advantageously emits electromagnetic radiation with a wavelength in a range from 380 nm to 315 nm. Radiation of this type is also referred to as so-called UV-A radiation. However, the use of UV-B radiation (315 nm-280 nm) and UV-C radiation (280 nm-100 nm) would also be conceivable.

According to a further advantageous embodiment, the first radiation source device comprises at least one radiation source. The at least one radiation source is preferably a light-emitting diode (LED). A large number of radiation sources is preferably provided. The first radiation source device preferably emits electromagnetic radiation with a wavelength in a range between 280 nm and 100 nm. Radiation of this type is referred to as UV-C radiation. With an advantageous use of UV-C radiation, this radiation would already have a corresponding effect on the air or the air flow. The short-wave UV radiation in particular has a strong bactericidal effect. It is absorbed by the DNA of the microorganisms and destroys their structure there. In this way, the living cells are inactivated. When using a first radiation source device which emits electromagnetic radiation in the UV-C range, a photocatalysis device is preferably not provided. In this case, the passage channel would be defined by the first radiation source device and a delimiting surface instead of the photocatalysis device.

According to a further advantageous embodiment, the display device comprises a second radiation source device. The second radiation source device preferably emits electromagnetic radiation. The electromagnetic radiation emitted by the second radiation source device is advantageously used to display information. The second radiation source device preferably comprises at least one radiation source. The at least one radiation source is preferably a light-emitting diode (LED). The second radiation source device preferably emits electromagnetic radiation in a wavelength range between 400 nm and 700 nm, i.e. light in the visible range. A large number of radiation sources is preferably provided. It would also be conceivable that the large number of radiation sources is subdivided into at least two subsets, the two subsets emitting electromagnetic radiation with different wavelengths. For example, a first subset could emit green light and a second subset could emit red light.

According to a further preferred embodiment, at least one display element is provided, which is irradiated with the electromagnetic radiation emitted by the second radiation source device. The electromagnetic radiation emitted by the second radiation source device is preferably background radiation for the display element. The display element could, for example, have lettering, symbols, etc., which are illuminated by the electromagnetic radiation. It would be conceivable that the display element consists of at least one decorative film. However, it would also be conceivable that the at least one display element comprises phosphorescent, luminescent or analogously emitting regions which are illuminated by the electromagnetic radiation emitted by the second radiation source device. By means of luminescence, phosphorescence or a similar mechanism, these regions of the display element emit corresponding visible radiation. The electromagnetic radiation emitted by the second radiation source device is therefore advantageously in a wavelength range which is matched to the phosphorescent, luminescent range. This wavelength range can extend from UV radiation to infrared radiation.

According to a further preferred embodiment, at least one radiation conduction device is provided. Such a radiation conduction device is preferably a light conductor. The radiation conduction device can comprise, for example, transparent components such as fibres, tubes or rods that transport radiation over short or long distances. The radiation conduction is achieved by reflection at the boundary surface of the conductor either through total reflection due to a lower refractive index of the medium surrounding the conductor or through mirroring of the boundary surface or through a suitable refraction gradient. The radiation conduction device can consist of optical fibres, for example polymer optical fibres. The radiation conduction device could preferably be a light-conducting component made of plastics material. A plastics material of this type is, for example, polymethyl methacrylate (PMMA) or polycarbonate. These components can preferably be shaped according to the spatial conditions in the domestic appliance. The electromagnetic radiation emitted by the second radiation source device can preferably be conducted to the at least one display element by means of the at least one radiation conduction device. If a plurality of subsets of radiation sources are advantageously provided, a plurality of radiation conduction devices can also be provided. At least one radiation conduction device is advantageously assigned to each subset of radiation sources. The plurality of radiation conduction devices can advantageously open into different display elements. Alternatively, the radiation conduction devices can advantageously open into only one display element. A radiation control device is preferably provided, by means of which the radiation from specific radiation conduction devices can be blocked or diverted. Thus, the beam path of the electromagnetic radiation can preferably be switched between different display devices.

According to a further advantageous embodiment, the first radiation source device and the second radiation source device are arranged on a support device. The support device preferably has a substantially plate-like design. The term "substantially" should be construed as including minor tolerance deviations. This should also apply accordingly to other uses of the term "substantially." The support device is preferably designed as a conductor board or a printed circuit board (PCB). It is advantageous in this case that the first radiation source device and the second radiation source device are arranged on opposite sides of the support device. Advantageously, only one plate-like support device is thus provided, on which both the first radiation source device and the second radiation source device are arranged. This provides an extremely compact design of the display apparatus having an integrated air treatment apparatus, which can be produced simply and inexpensively and can be arranged in a domestic appliance in the most space-saving way possible. The first radiation source device or one side of the support device which is equipped with the at least one radiation source of the first radiation source device is preferably arranged substantially opposite the photocatalysis device. The passage channel for the air or the air flow is advantageously provided between the first radiation source device or the side of the support device which is equipped with the at least one radiation source of the first radiation source device and the photocatalysis device. If no photocatalysis device is provided, it is advantageous that the passage channel for the air or the air flow is provided between the first radiation source device or the side of the support device which is equipped with the at least one radiation source of the first radiation source device and a delimiting surface. Such an arrangement results in optimal irradiation of the photocatalysis surface with the electromagnetic radiation. Furthermore, an optimal contact of the photocatalysis surface with the air flow can be ensured.

According to a further advantageous embodiment, the air treatment apparatus comprises a housing having at least one air inlet opening and at least one air outlet opening. The air flow preferably flows into the air treatment apparatus through the at least one air inlet opening and out of the air treatment apparatus through the at least one air outlet opening. The air flow preferably flows from the at least one air outlet opening into the container device. By means of the advantageous removal of a specific amount of air and the advantageous supply of a specific amount of air, an air circulation is created in the container device. By means of such an advantageous air circulation, a large part of the air in the container device, or substantially all of the air located in the container device, is successively supplied to the air treatment apparatus. The at least one air flow device advantageously generates a negative pressure at the air inlet opening. Preferably, an air flow into or through the at least one air inlet opening can be generated by means of this negative pressure. A corresponding overpressure is advantageously generated at the at least one air outlet opening by the air flow device. The at least one air flow device preferably conveys the air flow further to the passage channel, through said channel and subsequently through the at least one air outlet opening back into the container device. The air flow device advantageously comprises a rotor or a fan driven by a motor, preferably an electric motor.

According to a further advantageous embodiment, the air treatment apparatus comprises a closure device, by means of which the air treatment apparatus can be closed in a sealing manner. The air treatment apparatus can preferably be closed or separated from the container device in a sealing manner.

According to a further advantageous embodiment, the closure device preferably comprises at least one closure element which, in a closed position, closes the at least one air inlet opening and/or the at least one air outlet opening in a sealing manner. The closure device preferably comprises only one closure element which, in a closed position, closes the at least one air inlet opening and the at least one air outlet opening in a sealing manner. Alternatively, the closure device comprises two closure elements which, in a closed position, each close the at least one air inlet opening or the at least one air outlet opening in a sealing manner. The at least one closure element can preferably be moved from a closed position to an open position. It is also advantageous that the closure element can be moved from the open position to the closed position. In the open position of the at least one closure element, the air flow can preferably enter the at least one air inlet opening or exit through the at least one air outlet opening. The closure device preferably comprises at least one drive device which drives the at least one closure element. The movement is thus preferably carried out by means of the drive device. The drive device advantageously comprises an electric motor. It is of course also conceivable that the closure element can be moved into intermediate positions. Intermediate positions of this type can, for example, limit the entering and/or exiting air flow, for example by partially covering the at least one air inlet or air outlet opening. The air flow or the amount of air can thus advantageously be controlled.

The present object of the invention is also achieved by a domestic appliance, comprising at least one air treatment apparatus according to any of the embodiments described above. The domestic appliance can be equipped with all the features already described above in the scope of the display apparatus, individually or in combination with each other, and vice versa.

Such a domestic appliance advantageously comprises a housing and a container device provided therein. The display apparatus can preferably be arranged on or in the housing of the domestic appliance. Such a domestic appliance can advantageously be a refrigerator or a freezer, the articles for cooling or freezing being able to be brought into the container device. Such a domestic appliance can also be a dishwasher, a washing machine or some other domestic appliance. In the case of a domestic appliance in the form of a dishwasher or a washing machine, the container device is also referred to as a tub. The articles to be washed are placed in this tub. During the washing process, a washing liquid in the form of water mixed with a treatment agent is subsequently introduced into the tub.

The domestic appliance can comprise only one display apparatus or a plurality of, for example two, display apparatuses.

The housing of the domestic appliance preferably has a cubic or cuboid shape. The domestic appliance preferably has at least three side walls. The housing can comprise two lateral side walls. Furthermore, the housing can comprise a rear side wall. Finally, the housing can comprise a front side wall. Furthermore, it is advantageous that the domestic appliance has a closure apparatus by means of which the container device can be closed. The closure apparatus can be designed, for example, as a door which is integrated in the front side wall or is provided instead of a front side wall. Operating elements can optionally be provided for the user on the front side wall and/or on the closure apparatus. Operating elements of this type are, for example, program selection switches in a dishwasher. According to a preferred embodiment, the air treatment apparatus is arranged in or on the closure apparatus or the door of the housing of the domestic appliance.

According to a preferred embodiment, the housing of the domestic appliance comprises a closure apparatus by means of which it can be closed. The at least one display apparatus is preferably arranged in or on the closure apparatus. According to a further embodiment, the at least one air treatment apparatus is arranged in or on a side wall of the housing. The at least one display apparatus is advantageously provided on a lateral side wall of the housing. The at least one display apparatus is preferably provided on a rear side wall or rear wall of the housing.

At least one radiation conduction device is preferably provided, by means of which the electromagnetic radiation emitted by the second radiation source device can be guided to the at least one display element. The display element can be arranged on a component or part of the domestic appliance which is clearly visible to the user. The at least one display element can thus be provided in or on the same component of the domestic appliance as the remaining elements of the display apparatus or the air treatment apparatus. It would also be conceivable that the at least one display element is provided in or on a different component of the domestic appliance, such as the remaining elements of the display apparatus or the air treatment apparatus.

According to a preferred embodiment, at least one control device is provided. The air treatment apparatus is preferably activated in a first status of the display apparatus. The air treatment apparatus is preferably deactivated in a second status of the display apparatus. The components relating to the display are preferably activated in a third status of the display apparatus. In a fourth status of the display apparatus, the components relating to the display are preferably deactivated. The defined first and second statuses are independent of the defined third and fourth statuses. The display apparatus can accordingly be in the first and third status or in the first and fourth status. In other words, the components relating to the display can be activated and deactivated independently of the air treatment apparatus. Likewise, the air treatment apparatus can be activated or deactivated independently of the components relating to the display. The components for the display comprise at least the second radiation source arrangement, possibly a radiation control device and further components which are necessary or can be actuated for the display. The third or fourth status or the activation or deactivation can also be initiated independently of one another for specific subsets of radiation sources or radiation control devices. Accordingly, the lighting can be activated, deactivated or changed (changing the lighting from one subset to another subset) for specific display elements.

According to a further advantageous embodiment, a first status signal relating to the first status of the display apparatus can be received or generated by means of the control device. A second status signal relating to the second status of the display apparatus can preferably be received or generated by means of the control device. A third status signal relating to the third status of the display apparatus can preferably be received or generated by means of the control device. A fourth status signal relating to the fourth status of the display apparatus can preferably be received or generated by means of the control device.

According to a further advantageous embodiment, an input device is provided by means of which the status signals can be generated. The input device preferably sends the status signals to the control device. After receiving the status signal in each case, the control device preferably initiates the corresponding status of the display apparatus. The input device can preferably be operated manually. Accordingly, the input device can comprise, for example, buttons and/or switches and/or a touch screen. It would also be conceivable that the input device is suitable for processing voice inputs. Alternatively or cumulatively, the input device could also comprise gesture recognition for inputting commands by means of gestures. The input device can preferably receive the status signals from an external communication appliance of a user. The connection between the external communication appliance and the input device is preferably a wireless connection. An external communication appliance can be, for example, a smartphone, a tablet computer, a laptop or a similar appliance. A corresponding wireless connection can be, for example, an RFID (radio-frequency identification) connection, an NFC (near-field communication) connection, a WLAN connection or a cellular connection. Of course, further wireless connections or wired connections can also be used. Accordingly, the user can activate or deactivate the air treatment apparatus and/or the components relating to the display in a very convenient manner, for example via the smartphone.

However, the activation or deactivation of the display apparatus can also advantageously take place automatically. For this purpose, the control device itself preferably generates the status signal in each case. The status signals are subsequently processed by means of the control device in such a way that the corresponding status is initiated. The at least one control device preferably generates the status signals on the basis of sensor data from a sensor device. The sensor device preferably comprises at least one sensor which detects the load status in the container device. Such a sensor can, for example, be a weight sensor which detects the weight of the articles introduced. A sensor in the form of a camera system, which can recognise a load status, for example by image recognition, would also be conceivable. The first status could thus advantageously be triggered or the air treatment apparatus could be activated when a load is detected, for example in the case of a dishwasher in the form of dishes to be cleaned. Alternatively or cumulatively, the sensor device preferably comprises at least one sensor which detects specific gases in the air in the container device. Gases of this type can be, for example, those which cause an unpleasant odour. When such a gas is detected, the first status could preferably be triggered or the air treatment apparatus could be activated. After the removal of the gas, the second status could subsequently be triggered, or the air treatment apparatus could be deactivated. Furthermore, the sensor device could advantageously comprise at least one sensor which detects an opening of the closure apparatus. Thus, when opening the closure apparatus, the second status could advantageously be triggered, or the air treatment apparatus could be deactivated. After closing the closure apparatus, the first status could advantageously be triggered, or the air treatment apparatus could be activated. It would be conceivable that at least one display element is arranged on an inner wall of the closure apparatus. Thus, when opening the closure apparatus, the third status could be initiated, or the components for the display could be activated. Accordingly, when closing the closure apparatus, the fourth status could be initiated, or the components for the display could be deactivated. Furthermore, it is conceivable that the sensor device advantageously comprises at least one sensor which detects the ambient light conditions. The third status could thus be initiated when the ambient light falls below a predetermined limit value.

A status signal can preferably also be generated or received when a specific program of the domestic appliance is started, for example when a washing program is started. This can take place by means of the control device or also by means of a further control device.

The display apparatus can advantageously be used to display specific statuses of the domestic appliance. For example, a load status, a specific operating program or a specific error in a status of the domestic appliance can be displayed by changing the lighting of the at least one display element.

According to a further advantageous embodiment, a timer device is provided. Such a timer device can preferably be integrated in the control device or also be provided as a further device in the domestic appliance. The status signals can advantageously be generated on the basis of a predetermined point in time or a predetermined time interval. The point in time of the activation of the statuses can thus advantageously be predetermined.

The control device advantageously comprises a memory device in which specific sequence programs are stored. Sequence programs of this type can comprise the sequential control of specific devices, such as the first radiation source device, the second radiation source device, a radiation control device, the air flow device, etc. Likewise, the intensity of the activation of these devices can advantageously be provided in such a sequence program. The photocatalytic reaction, for example, can be controlled by advantageously controlling the operating current of the first radiation source device. Likewise, the air flow speed can be controlled by an advantageous control of the air flow device.

The present object of the invention is also achieved by a method for controlling a domestic appliance or a display device. The method can be equipped with all the features already described above in the scope of the apparatus, individually or in combination with each other, and vice versa.

BRIEF DESCRIPTION OF THE DRAWINGS

Further advantages, aims and properties of the present invention will be explained with reference to the following description of the accompanying drawings. Similar components may have the same reference signs in the various embodiments.

In the drawings.

DETAILED DESCRIPTION

Figure 2:
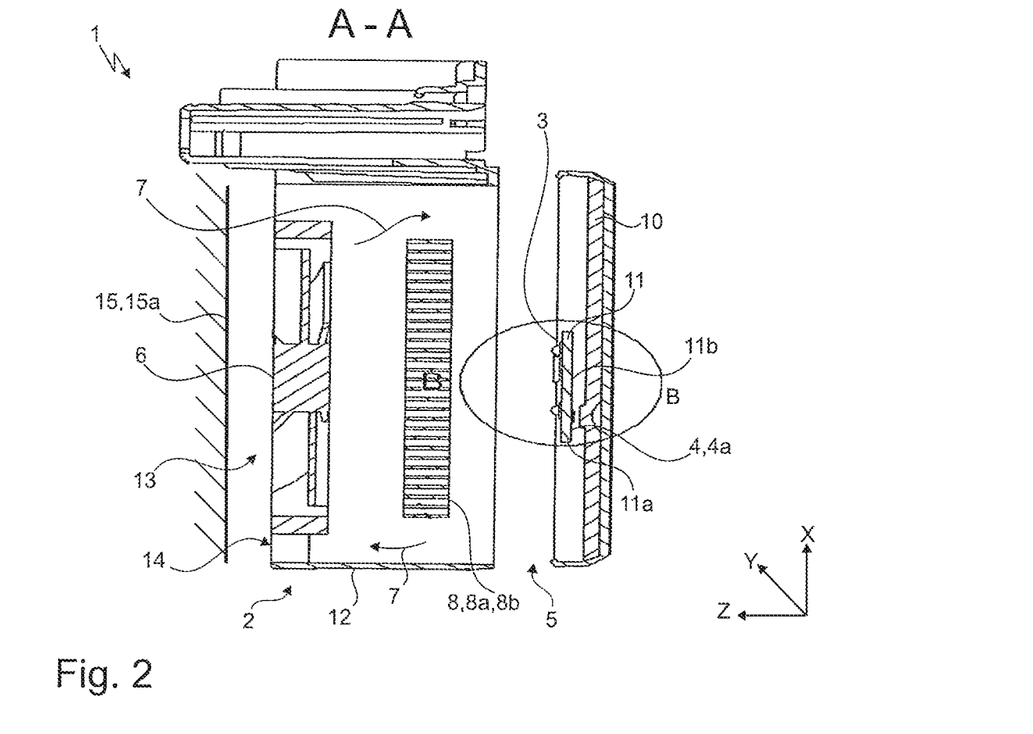
FIG. 2 shows a display apparatus according to one embodiment.
Figure 3:
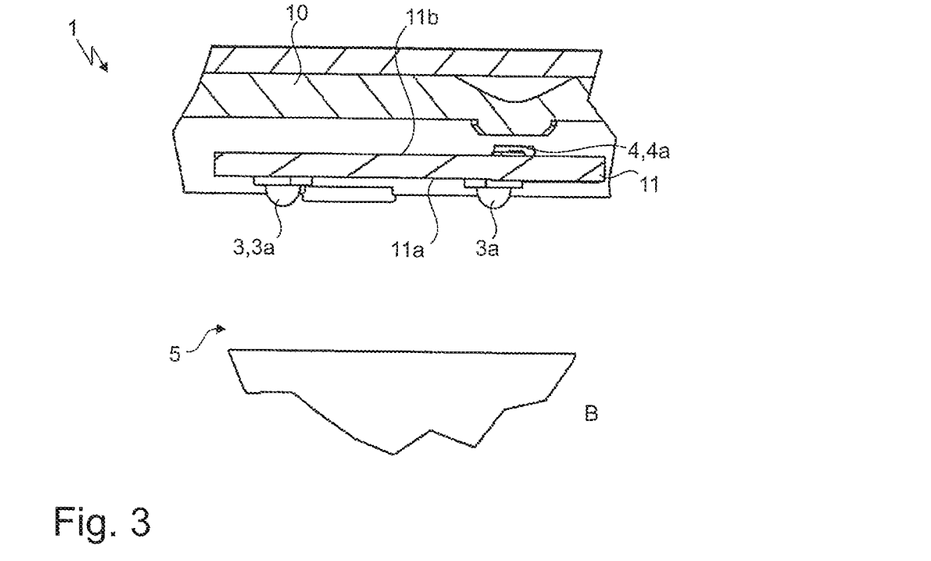
FIG. 3 shows a display apparatus according to one embodiment.
Figure 4:
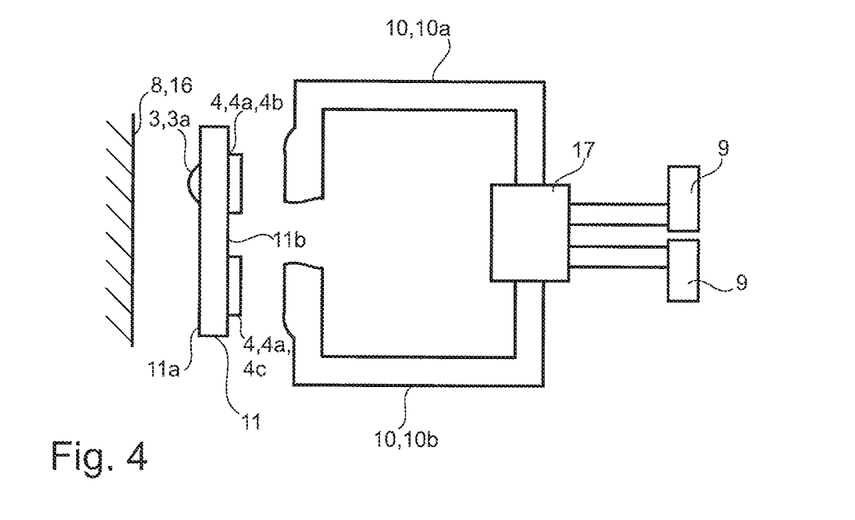
FIG. 4 shows a display apparatus according to one embodiment.

In FIGS. 2 to 4, a display apparatus 1 for a domestic appliance 100 is shown, at least one air treatment apparatus 2 being integrated in the display apparatus 1, the at least one air treatment apparatus 2 comprising a first radiation source device 3 by means of which a fluid, in particular air, passing through a passage channel 5 can be treated.

Figure 1:
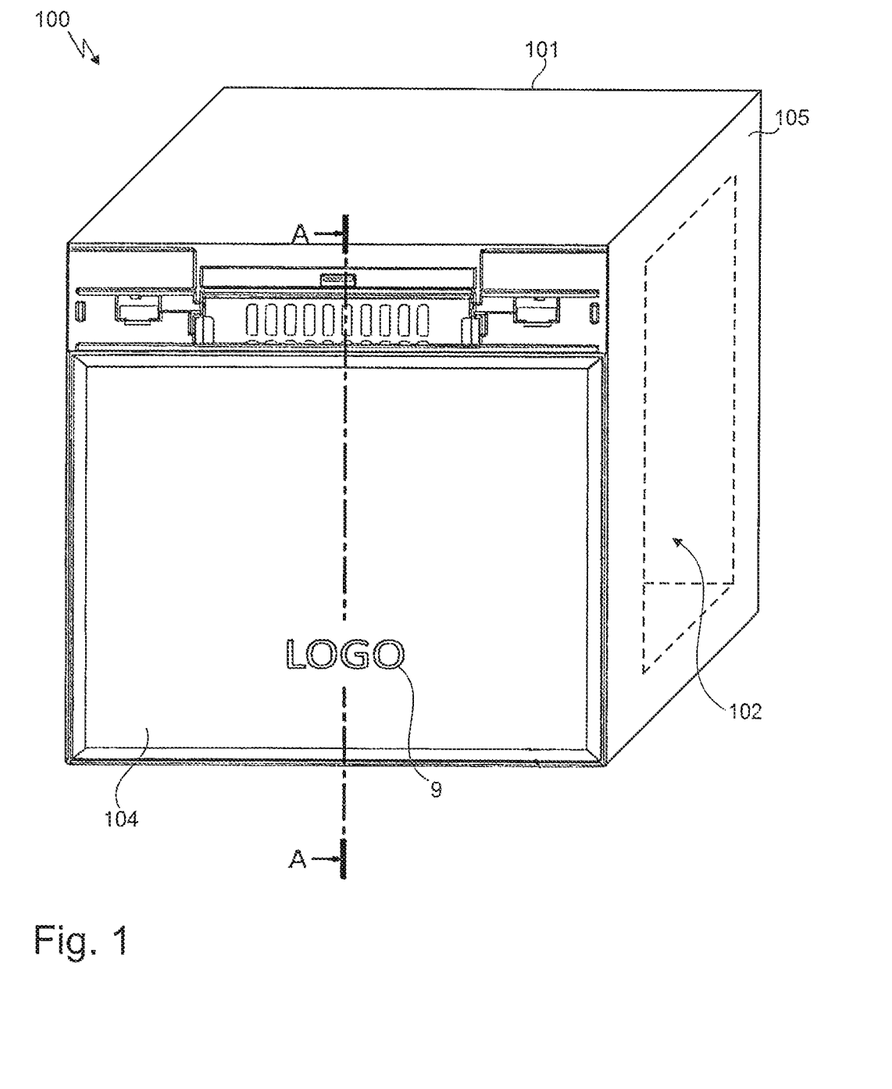
FIG. 1 shows a domestic appliance, comprising at least one air treatment apparatus according to one embodiment.

FIG. 1 shows a domestic appliance 100 comprising at least one display apparatus 1. The domestic appliance 100 can be a refrigerator, a freezer, a dishwasher, a washing machine or the like. The domestic appliance 100 comprises a housing 101 and a container device 102 provided therein. The display apparatus 1 can be arranged on or in the housing 101 of the domestic appliance 100.

At least one air flow device 6 is provided, by means of which an air flow 7 into and/or out of the air treatment apparatus 2 can be generated, the air flow 7 passing through the passage channel 5. Furthermore, an air flow 7 from and/or into the container device 102 can be generated by means of the at least one air flow device 6. Accordingly, the air in the container device 102 can be treated, cleaned or disinfected.

The display apparatus 1 having the integrated air treatment apparatus 2 comprises a housing 12 which extends along a height axis Z, a longitudinal axis X and a width axis Y. This can be seen clearly in FIG. 2. At least one air inlet opening 13 and at least one air outlet opening 14 are provided on the housing 12. The housing 12 preferably consists of a plastics material or a metal. The air flow 7 flows into the housing 12 through the at least one air inlet opening 13 and out of the housing 12 through the at least one air outlet opening 14. Accordingly, the air flow 7 flows from the container device 102 into the at least one air inlet opening 13 and from the at least one air outlet opening 14 into the container device 102. Within the air treatment apparatus 2, the air flow 7 flows through the passage channel 5 and subsequently to the at least one air outlet opening 14. The air flow 3 entering the container device 102 is thus cleaned or processed. The at least one air flow device 6 generates a negative pressure at the at least one air inlet opening 13, by means of which the air flow 7 into the at least one air inlet opening 13 can be generated. Correspondingly, an overpressure is generated at the at least one air outlet opening 14. Furthermore, a closure device 15 can be provided, by means of which the air treatment apparatus 2 can be closed or separated from the container device 102 in a sealing manner. Thus, during the washing cycle of the domestic appliance, the interior of the air treatment apparatus 2 is protected from the washing liquid. The closure device 15 comprises at least one closure element 15a which, in a closed position, closes the at least one air inlet opening 13 and/or the at least one air outlet opening 14 in a sealing manner. At least one closure element 15a can be moved from a closed position to an open position, and vice versa. In the closed position, the at least one air inlet opening 13 and the at least one air outlet opening 14 are closed in a sealing manner. The closure device 15 comprises at least one drive device which drives the at least one closure element 15a (not shown). The drive device can, for example, be an electric motor which moves the closure element 15a via at least one force transmission means, for example a transmission.

The air treatment apparatus 2 extends along a height axis Z, a width axis Y and a longitudinal axis X. The air treatment apparatus 2 comprises a passage channel 5 for the air flow 7, a first radiation source device 3. According to one embodiment, the air treatment apparatus 2 further comprises a photocatalysis device 8. The first radiation source device 3 emits electromagnetic radiation. The photocatalysis device 8 can be exposed to at least part of the electromagnetic radiation in order to produce a photocatalytic reaction. The photocatalysis device 8 comprises a photocatalytic surface 8a which comprises at least one photocatalytic material. The photocatalytic material is a semiconductor, preferably titanium(IV) oxide, $TiO_2$. The photocatalytic surface 8a comprises regions 8b having the photocatalytic material. However, other configurations of the photocatalytic surface 8a are also conceivable. When using titanium dioxide, it is advantageous that the first radiation source device 3 emits electromagnetic radiation with a wavelength of less than 400 nm, preferably in a range from 380 nm to 315 nm. The radiation source device 3 comprises at least one radiation source 3a, the at least one radiation source 3a being a light-emitting diode (LED) or a UV LED. The radiation source device 3 comprises a large number of radiation sources 3a with a total number Ntot of radiation sources 3a. The at least one radiation source 3a is arranged on the first side 11a of a support device 11. The support device 11 has a substantially plate-like design. The first side 11 a of the support device 11 is arranged substantially opposite the photocatalysis device 8. The passage channel 5 for the air flow 7 is provided between the support device 11 and the photocatalysis device 8.

According to a further embodiment, a photocatalysis device 8 is not provided. The passage channel 5 is therefore defined by a delimiting surface 16 and the support device 11, the first side 11a of the support device 11 being arranged substantially opposite the one delimiting surface 16. In this embodiment, the first radiation source device 3 comprises at least one radiation source 3a, the at least one radiation source 3a being a light-emitting diode (LED). The first radiation source device 3 emits electromagnetic radiation with a wavelength in a range between 280 nm and 100 nm.

The display device 1 comprises a second radiation source device 4. The second radiation source device 4 emits electromagnetic radiation which is used or serves to display information. The second radiation source device 4 comprises at least one radiation source 4a, which is advantageously designed as a light-emitting diode (LED). The second radiation source device 4 preferably emits electromagnetic radiation in a wavelength range between 400 nm and 700 nm. The first radiation source device 3 and the second radiation source device 4 are arranged on opposite sides 11a, 11b of the support device 11. The first radiation source device 3 is arranged substantially opposite the photocatalysis device 8 or the delimiting surface 16, the passage channel 5 for the air flow 7 being provided between the support device 11 and the photocatalysis device 8 or the delimiting surface 16.

At least one display element 9 is provided, which is irradiated with the electromagnetic radiation emitted by the second radiation source device 4. At least one radiation conduction device 10 is provided in this case, by means of which the electromagnetic radiation emitted by the second radiation source device 4 can be conducted to the at least one display element 9. Such a radiation conduction device 10 is preferably a light conductor into which at least part of the electromagnetic radiation emitted by the second radiation source 4 is coupled. This can be seen in FIGS. 3 and 4. The support device 11 is arranged in a first portion 12a of the housing 12, which can be connected to the second housing portion 12b by means of a force and/or a form-fitting connection, preferably by means of a snap connection. This is shown in FIG. 3. The coupling of the electromagnetic radiation into the radiation conduction device 10 is provided in the first portion 12a of the housing 12. The at least one display element 9 can have regions which are lettering, a logo, a symbol, or the like. It would also be conceivable that part of the electromagnetic radiation emitted by the second radiation source 4 serves as background lighting of a component of the domestic appliance 100. Such a component can be, for example, a door 104 or an interior lining.

The second radiation source device 4 preferably comprises a plurality of radiation sources 4a. The plurality of radiation sources 4a can preferably be divided into at least two subsets 4b, 4c. These subsets and radiation sources 4, 4a, 4b, 4c can be designed in such a way that they emit electromagnetic radiation with different wavelengths or colours. A plurality of radiation conduction devices 10, 10a, 10b can be provided, into which the emitted electromagnetic radiation is coupled in each case. In FIG. 4, for example, an embodiment having subsets 4b, 4c is shown, the electromagnetic radiation of the first subset 4b being coupled into the first radiation conduction device 10, 10a and the electromagnetic radiation of the second subset 4c being coupled into the second radiation conduction device 10, 10b.

The plurality of radiation conduction devices 10, 10a, 10b can advantageously open into different display elements 9. Alternatively, the radiation conduction devices 10, 10a, 10b can advantageously open into only one display element 9. Preferably, a radiation control device 17 is provided, by means of which the radiation from specific radiation conduction devices 10, 10a, 10b can be blocked or diverted. Thus, the beam path of the electromagnetic radiation can preferably be switched between different display devices 9. Likewise, a subset of radiation sources 4, 4a, 4b, 4c could illuminate a single display device 9, while the radiation from the further subset of radiation sources 4, 4a, 4b, 4c is blocked.

A domestic appliance 100 is shown in FIG. 1. The housing 101 of the domestic appliance 100 can comprise a closure apparatus 104, for example a door, by means of which the container device 102 can be closed. At least one display apparatus 1 having an integrated air treatment apparatus 2 can be arranged in or on the closure apparatus 104. The domestic appliance 100 can have a substantially cubic or cuboid shape and comprise two lateral side walls 105 and a rear side wall 105 or also a rear wall, which is preferably opposite the closure apparatus 104. Finally, the housing may comprise a front side wall 105. The closure apparatus 104 can be designed, for example, as a door which is integrated in the front side wall 105 or is provided instead of a front side wall 105. Operating elements can optionally be provided for the user on the front side wall and/or on the closure apparatus 104. Operating elements of this type are, for example, program selection switches in a dishwasher. The at least one display apparatus 1 having an integrated air treatment apparatus 2 can be arranged in or on a side wall 105 of the housing 101. The air treatment apparatus 1 can thus be arranged in or on a lateral side wall 105 or a rear side wall 105.

Figure 5:
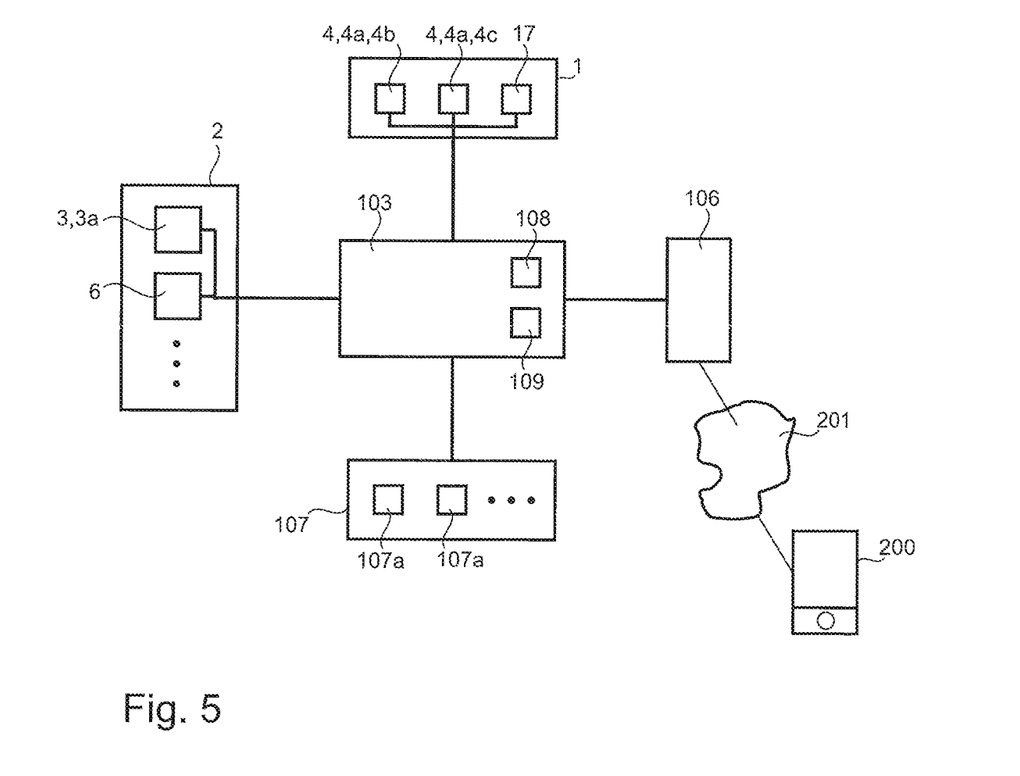
FIG. 5 shows a basic circuit diagram of a domestic appliance according to one embodiment.

FIG. 5 shows a basic circuit diagram for a domestic appliance 100 having at least one display apparatus 1 having an integrated air treatment apparatus 2. Accordingly, a control device 103 is provided which can be assigned to the domestic appliance 100 or the display apparatus 1. The control device 103 is connected by signals to the air treatment apparatus 2 or to the first radiation source device 3, the air flow device 2, and optionally the drive device for the closure element 13. A first status signal relating to the first status of the display apparatus 1 can be received or generated by means of the control device 103. Furthermore, a second status signal relating to the second status of the display apparatus 1 can be received or generated by means of the control device 103. Furthermore, a third status signal relating to the third status of the display apparatus 1 can be received or generated by means of the control device 103, a fourth status signal relating to the fourth status of the display apparatus 1 being able to be received or generated by means of the control device (103). In the first status of the display apparatus 1, the air treatment apparatus 2 is activated. In the one second status of the display apparatus 1, the air treatment apparatus 2 is deactivated. In a third status of the display apparatus 1, the components relating to the display 4, 4a, 4b, 4c, 17 are activated. In a fourth status of the display apparatus 1, the components relating to the display 4, 4a, 4b, 4c, 17 are deactivated. The defined first and second statuses are independent of the defined third and fourth statuses. The display apparatus 1 can accordingly be in the first and third status or in the first and fourth status. In other words, the components relating to the display 4, 4a, 4b, 4c, 17 can be activated and deactivated independently of the air treatment apparatus 2. Likewise, the air treatment apparatus 2 can be activated or deactivated independently of the components relating to the display 4, 4a, 4b, 4c, 17. The third or fourth status or the activation or deactivation can also be initiated independently of one another for specific subsets of radiation sources 4, 4a, 4b, 4c or radiation control devices 17. Accordingly, the lighting can be activated, deactivated or changed (changing the lighting from one subset to another subset) for specific display elements 9.

In the second status, the display device 1 having an integrated air treatment apparatus 2 can optionally be closed in a sealing manner with respect to the container device 102 by means of the closure device 15. In the second status, the at least one closure element 15a is in the closed position. Likewise, in the second status, the air flow device 6 can be deactivated by means of the control device 103. In one embodiment of the domestic appliance 100 in the form of a dishwasher, a washing machine or the like, the washing liquid is introduced into the container device 102 or into the tub in the second status. Due to the sealing closure of the display device 1 having an integrated air treatment apparatus 2 with respect to the container device 102, the washing liquid cannot penetrate into the air treatment apparatus 1.

The control device 103 is connected by signals to at least one input device 106, by means of which the status signals can be generated. The input device 106 sends the status signals to the at least one control device 103, as a result of which the corresponding statuses are initiated. The input device 106 can preferably be operated manually. Accordingly, the input device 106 can comprise, for example, buttons and/or switches and/or a touch screen. The input device 106 can preferably receive the first status signal and/or the second status signal from an external communication appliance 200 of a user. The connection between the external communication appliance and the input device is preferably a wireless connection 201. An external communication appliance 200 can be, for example, a smartphone, a tablet computer, a laptop or a similar appliance. A corresponding wireless connection 201 can be, for example, an RFID (radio-frequency identification) connection, an NFC (near-field communication) connection, a WLAN connection or a cellular connection. Of course, further wireless connections or wired connections can also be used.

However, the display apparatus 1 having an integrated air treatment apparatus 2 can also be activated or deactivated automatically. For this purpose, the control device 103 itself preferably generates the status signal in each case. The status signals are subsequently processed by means of the control device 103 in such a way that the corresponding status is initiated. The at least one control device 103 preferably generates the status signals on the basis of sensor data from a sensor device 107. The sensor device 107 preferably comprises at least one sensor 107a which detects the loading status in the container device. Such a sensor 107a can, for example, be a weight sensor which detects the weight of the articles introduced. A sensor 107a in the form of a camera system, which can recognise a load status, for example by image recognition, would also be conceivable. The first status could thus be triggered or the air treatment apparatus 2 could be activated when a load is detected, for example in the case of a dishwasher in the form of dishes to be cleaned. Alternatively or cumulatively, the sensor device 107 preferably comprises at least one sensor 107a which detects specific gases in the air in the container device 102. Gases of this type can be, for example, those which cause an unpleasant odour. When such a gas is detected, the first status could preferably be triggered or the air treatment apparatus 2 could be activated. After the removal of the gas, the second status could subsequently be triggered, or the air treatment apparatus 2 could be deactivated. Furthermore, the sensor device 107 could advantageously comprise at least one sensor 107a, which detects an opening of the closure apparatus 104 or the door of the domestic appliance 100. Thus, when opening the closure apparatus 104, the second status could advantageously be triggered, or the air treatment apparatus 2 could be deactivated. After closing the closure apparatus 104, the first status could be triggered, or the air treatment apparatus 2 could be activated. It would be conceivable that the at least one display element 9 is arranged on an inner wall of the closure apparatus 102. Thus, when opening the closure apparatus 102, the third status could be initiated or the components for the display 4, 4a, 4b, 4c, 17 could be activated. Accordingly, when closing the closure apparatus 104, the fourth status could be initiated, or the components for the display 4, 4a, 4b, 4c, 17 could be deactivated. Furthermore, it is conceivable that the sensor device 107 advantageously comprises at least one sensor 107a which detects the ambient light conditions. The third status could thus be initiated when the ambient light falls below a predetermined limit value. A status signal can preferably also be generated or received when a specific program of the domestic appliance is started, for example when a washing program is started. This can take place by means of the control device 103 or also by means of a further control device.

The display apparatus 1 can advantageously be used to display specific statuses of the domestic appliance 100. For example, a load status, a specific operating program or a specific error in a status of the domestic appliance can be displayed by changing the lighting of the at least one display element 9. According to a further embodiment, a timer device 108 is provided. Such a timer device 108 can preferably be integrated in the control device 103 or also be provided as a further device in the domestic appliance 100. The status signals can advantageously be generated on the basis of a predetermined point in time or a predetermined time interval. The point in time of the activation of the statuses can thus advantageously be predetermined. The control device 103 advantageously comprises a memory device 109 in which specific sequence programs are stored. Sequence programs of this type can comprise the sequential control of specific devices, such as the first radiation source device 3, the second radiation source device 4, a radiation control device 17, the air flow device 6, etc. Likewise, the intensity of the activation of these devices can advantageously be provided in such a sequence program. The photocatalytic reaction, for example, can be controlled by advantageously controlling the operating current of the first radiation source device 3. Likewise, the air flow speed can be controlled by an advantageous control of the air flow device 6.

The applicant reserves the right to claim all the features disclosed in the application documents as substantial to the invention, provided that these are novel individually or in combination over the prior art. It is further pointed out that features have also been described in the individual drawings, which in themselves can be advantageous. A person skilled in the art will immediately recognise that a specific feature described in one drawing can also be advantageous without adopting further features from said drawing. A person skilled in the art will further recognise that advantages can also result from a combination of a plurality of features shown in individual or in different drawings.

LIST OF REFERENCE SIGNS

1 Display apparatus
2 Air treatment apparatus

3 First radiation source device
3a Radiation source
4 Second radiation source device
4a Radiation source
4b First subset of radiation sources
4c Second subset of radiation sources
5 Passage channel
6 Air flow device
7 Air flow
8 Photocatalysis device
8a Photocatalytic surface
8b Regions of the photocatalytic surface having the photocatalytic material
9 Display element
10 Radiation conduction device
11 Support device
11a First side of the support device
11b Second side of the support device
12 Housing of the air treatment apparatus
12a First portion of the housing
12b Second portion of the housing
13 Air inlet opening
14 Air outlet opening
15 Closure device
15a Closure element
16 Delimiting surface
17 Radiation control device
100 Domestic appliance
101 Housing
102 Container device
103 Control device
104 Closure apparatus
105 Side wall
106 Input device
107 Sensor device
107a Sensor
108 Timer device
109 Memory device
200 Communication appliance
201 Wireless connection
X Longitudinal axis of the display apparatus
Y Width axis of the display apparatus
Z Height axis of the display apparatus

What is claimed is:

1. A display apparatus for a domestic appliance, comprising:
at least one air treatment apparatus integrated in the display apparatus, the at least one air treatment apparatus comprising a first radiation source device by which a fluid, in particular air, passing through a passage channel can be treated, wherein the first radiation source device and a second radiation source device are arranged on a support device, the support device having a plate-like design, the first radiation source device and the second radiation source device being arranged on opposite surfaces of the support device, the first radiation source device being arranged substantially opposite a photocatalysis device, and the passage channel being provided between the support device and the photocatalysis device.

2. The display apparatus according to claim 1, further comprising:
at least one air flow device, by which, an air flow of at least one of: into or out of the at least one air treatment apparatus can be generated, the air flow passing through the passage channel.

3. The display apparatus according to claim 2, wherein the at least one air treatment apparatus comprises a housing having at least one air inlet opening and at least one air outlet opening, the air flow flowing into the at least one air treatment apparatus through the at least one air inlet opening and out of the at least one air treatment apparatus through the at least one air outlet opening, the at least one air flow device generating a negative pressure at the at least one air inlet opening, the air flow into the at least one air inlet opening being able to be generated by means of this negative pressure.

4. The display apparatus according to claim 1, wherein the first radiation source device emitting electromagnetic radiation, the photocatalysis device being able to be exposed to at least one part of the electromagnetic radiation in order to produce a photocatalytic reaction, the photocatalysis device comprising a photocatalytic surface which comprises at least one photocatalytic material, the at least one photocatalytic material being a semiconductor, the at least one photocatalytic material being titanium(IV) oxide, TiO2.

5. The display apparatus according to claim 1, wherein the first radiation source device comprises at least one radiation source, the at least one radiation source being a light-emitting diode (LED), the first radiation source device emitting electromagnetic radiation with a wavelength of less than 400 nm.

6. The display apparatus according to claim 5, wherein the first radiation source device emits electromagnetic radiation with the wavelength in a range between 280 nm and 100 nm.

7. The display apparatus according to claim 5, wherein the first radiation source device emits electromagnetic radiation with the wavelength in a range from 380 nm to 315 nm.

8. The display apparatus according to claim 1, wherein the second radiation source device emits electromagnetic radiation which is used to display information, the second radiation source device comprising at least one radiation source, the at least one radiation source being a light-emitting diode (LED), the second radiation source device emitting electromagnetic radiation in a wavelength range between 400 nm and 700 nm.

9. The display apparatus according to claim 8, wherein at least one display element is provided, which is irradiated with the electromagnetic radiation emitted by the second radiation source device, at least one radiation conduction device is provided, the electromagnetic radiation emitted by the second radiation source device being able to be conducted to the at least one display element by the at least one radiation conduction device.

10. A domestic appliance comprising at least one display apparatus according to claim 1, the domestic appliance comprising a housing and a container device provided therein.

11. The domestic appliance according to claim 10, wherein the housing of the domestic appliance comprises a closure apparatus by which the container device can be closed, the at least one display apparatus being arranged in or on the closure apparatus.

12. The domestic appliance according to claim 10, wherein at least one control device is provided, an air treatment apparatus being activated in a first status of the display apparatus, the air treatment apparatus being deactivated in a second status of the at least one display apparatus, components relating to the at least one display apparatus being activated in a third status of the at least one display apparatus, the components relating to the at least one display apparatus being deactivated in a fourth status of the at least one display apparatus.

13. The domestic appliance according to claim 12, wherein a first status signal relating to the first status of the display apparatus can be received or generated by the at least one control device, a second status signal relating to the second status of the display apparatus being able to be received or generated by the at least one control device, a third status signal relating to the third status of the display apparatus being able to be received or generated by the at least one control device, a fourth status signal relating to the fourth status of the display apparatus being able to be received or generated by the at least one control device.

\* \* \* \* \*